United States Patent
Kumar et al.

(10) Patent No.: US 11,607,646 B2
(45) Date of Patent: Mar. 21, 2023

(54) PROCESS FOR $CO_2$ CAPTURE FROM GASEOUS STREAMS

(71) Applicant: INDIAN OIL CORPORATION LIMITED, Mumbai (IN)

(72) Inventors: Manoj Kumar, Faridabad (IN); Prakash Chandra Sahoo, Faridabad (IN); Suresh Kumar Puri, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 803 days.

(21) Appl. No.: 16/545,578

(22) Filed: Aug. 20, 2019

(65) Prior Publication Data
US 2020/0070091 A1 Mar. 5, 2020

(30) Foreign Application Priority Data
Aug. 29, 2018 (IN) .............................. 201821032404

(51) Int. Cl.
*B01D 53/84* (2006.01)
*B01J 20/22* (2006.01)
(Continued)

(52) U.S. Cl.
CPC ............. *B01D 53/84* (2013.01); *B01D 53/62* (2013.01); *B01J 20/22* (2013.01); *B01J 20/24* (2013.01);
(Continued)

(58) Field of Classification Search
CPC ................ B01D 53/84; B01D 2251/95; B01D 2255/804; B01D 2257/504;
(Continued)

(56) References Cited

U.S. PATENT DOCUMENTS 9,321,005 B2 4/2016 Broderick et al.
9,533,258 B2 1/2017 Fradette et al.
(Continued)

FOREIGN PATENT DOCUMENTS

WO 2011/014955 A1 2/2011
WO 2012/038865 A1 3/2012
(Continued)

*Primary Examiner* — Anita Nassiri-Motlagh
(74) *Attorney, Agent, or Firm* — Maschoff Brennan

(57) ABSTRACT

A process for selective capture of $CO_2$ from gaseous mixture comprising of: (a) spraying a bio-amine cluster; (b) capturing $CO_2$ through bio-amine cluster; and (c) desorption of $CO_2$ through solar assisted electro de-amination, wherein the bio-amine cluster is comprises of: an amine cluster comprising of a quaternary Isobutylamine (IB) with amine terminated Poly(L-lactide) as the chelating agent; a cluster stabilizing agent; a cluster micelle stabilizing agent; and a carbonic anhydrase (CA) functionalized matrix in 0.05-0.2 wt % of total wt % of bio-amine cluster and wherein the CA is obtained from a source selected from the group consisting of *Bacillus thermoleovorans*, *Pseudomonas fragi*, *Bacillus stearothermophilus* and *Arthrobacter* sp. and a process for production of bio-amine cluster.

19 Claims, 3 Drawing Sheets

Figure 1:
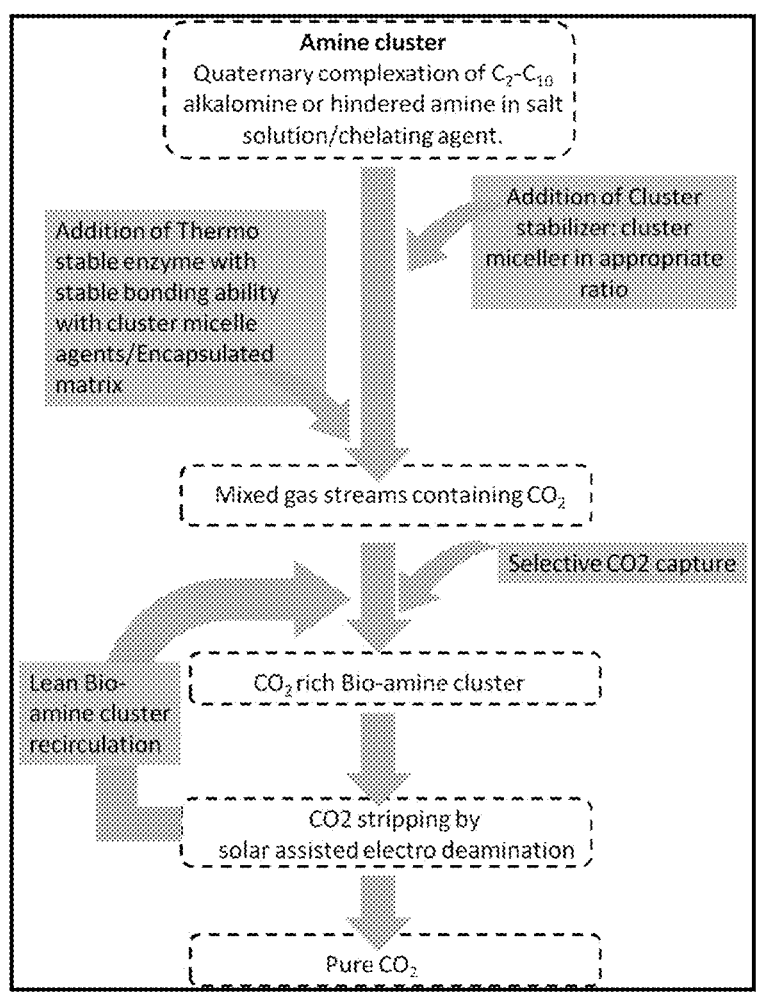

(51) Int. Cl.
*B01J 20/26* (2006.01)
*B01J 20/24* (2006.01)
*B01J 20/34* (2006.01)
*B01J 20/30* (2006.01)
*C12N 9/88* (2006.01)
*C12P 13/00* (2006.01)
*B01D 53/62* (2006.01)
*C01B 32/50* (2017.01)

(52) U.S. Cl.
CPC ......... *B01J 20/265* (2013.01); *B01J 20/3085* (2013.01); *B01J 20/3425* (2013.01); *B01J 20/3441* (2013.01); *C01B 32/50* (2017.08); *C12N 9/88* (2013.01); *C12P 13/001* (2013.01); *C12Y 402/01001* (2013.01); *B01D 2251/95* (2013.01); *B01D 2255/804* (2013.01); *B01D 2257/504* (2013.01); *B01D 2258/06* (2013.01)

(58) Field of Classification Search
CPC .... B01D 2258/06; B01D 53/62; C01B 32/50; B01J 20/22; B01J 20/24; B01J 20/265; B01J 20/3085; B01J 20/3425; B01J 20/3441; C12N 9/88; C12Y 402/01001
USPC ......................................................... 435/243
See application file for complete search history.

(56) References Cited

U.S. PATENT DOCUMENTS

| | | |
|---|---|---|
| 9,670,237 B2 | 6/2017 | Dai et al. |
| 2005/0129598 A1 | 6/2005 | Chinn et al. |
| 2012/0009652 A1* | 1/2012 | Alvizo ................ B01D 53/62 435/254.11 |
| 2014/0113346 A1* | 4/2014 | Ge ........................ C12N 9/88 435/174 |

FOREIGN PATENT DOCUMENTS

| | | |
|---|---|---|
| WO | 2013/159228 A1 | 10/2013 |
| WO | 2014/118633 A2 | 8/2014 |
| WO | 2016/027164 A1 | 2/2016 |

\* cited by examiner

PROCESS FOR $CO_2$ CAPTURE FROM GASEOUS STREAMS

FIELD OF THE INVENTION

The present invention relates to a process for obtaining purified carbon dioxide from any stream containing the mixture of gases. More specifically the invention relates to the field of reduction of $CO_2$ emission particularly by selective $CO_2$ capture. The invention further provides a process which involves a bio-amine cluster system and catalyst for selective capturing of $CO_2$ from any gaseous stream.

BACKGROUND OF THE INVENTION

Methods for capturing carbon dioxide ($CO_2$) as the main greenhouse gas are attaining a global concern due to its adverse environmental impact. Reactive absorption with aqueous solutions of amines in an absorber/stripper loop is the most practiced technology for post-combustion $CO_2$ capture (PCC). The main barrier that remains unresolved is the low loading capacity of the solvent, selectivity and huge energy requirement for solvent regeneration in the stripper. In fact, improvement of $CO_2$ absorption and reduction of solvent regeneration energy is the focus of most of the amine-based PCC research currently being performed globally.

EP2618914 A1 discloses a solvent composition for recovery of carbon dioxide from a gaseous mixture, comprising diethanolamine, piperazine or its derivative, an alkali salt, along with cupric carbonate. The disclosure relates to improved solvent formulations that utilize less energy and increased carbon capture efficiency. The disclosure also addresses the high $CO_2$ loading capacity and energy requirement over the existing carbon dioxide capture solvent.

WO2016027164 A1 describes methods and compositions for physical solvent carbon capture. The solvents may include an aqueous mixture of 2-amino-2-methylproponol, 2-piperazine-1-ethylamine, diethylenetriamine, 2-methylamino-2-methyl-1-propanol and potassium carbonate or potassium carbonate buffer salt. The solvent may also contain less than about 75% by weight of dissolving medium (i.e., water) and may have a single liquid phase.

WO2014118633 A3 describes a solvent for recovery of carbon dioxide from the gaseous mixture, having alkanolamine, reactive amines acting as promoter or activators, glycol and a carbonate buffer. It also describes a solvent for recovery of carbon dioxide from the gaseous mixture, having alkanolamine, reactive amines acting as promoter or activators, sulfolane and a carbonate buffer. One specific solvent contains less than about 75% by weight of water and has a single liquid phase.

However, $CO_2$ loading capacity in these processes is selectively limited by the concentration of the amine solution. Also, the regenerated amine solution, although lean in $CO_2$, still contains some absorbed $CO_2$, which reduces its capacity. Thus, the effective, steady-state $CO_2$ removal rate is further lowered. So, higher circulation rates are required for removal of $CO_2$ to desired levels. Further, the solvent can corrode low alloy steel such as carbon steel. Thus, only amine solutions (in water) with carefully controlled solution strengths are used to minimize corrosion of the absorption column, piping, and pumps. However, this diluted concentration requires higher circulation rates to achieve the desired $CO_2$ removal. High circulation rates require larger process equipment (capital expense), increased reboiler duty (energy/operating expense) and increased pumping costs (energy/operating expense).

Degradation of solvent is another issue. Amines may react with $CO_2 H_2 S$, NOx, or pollutants, or $O_2$ etc. to form various different products that are not reversible in the regeneration step. Amines may also degrade thermally and by oxidative route. Disposal of the degradation products may also be a concern. Furthermore, energy is also required to generate steam within the amine regenerator to strip the $CO_2$ from the solvent. For some strongly-absorbing amines and for large circulation rates, the energy requirement can be very high and represents a significant operating expense.

U.S. Pat. No. 9,321,005 B2 describes an invention comprises an absorbent composition and process for purification of gaseous mixtures. The composition comprises a mixture of a physical absorption solvent and an ionic liquid. It was found that the mixtures provided improved absorption of a gas component, such as carbon dioxide when compared to physical absorption solvents.

US20050129598 A1 describes a process and method for separating $CO_2$ from a gaseous stream such as natural gas. An ionic liquid comprising an anion having a carboxylate function is used as an adsorbent to selectively complex the $CO_2$ yielding a gaseous stream with a greatly reduced $CO_2$ content. The ionic liquid can then be readily regenerated and recycled.

U.S. Pat. No. 9,670,237 B2 discloses an ionic liquid composition containing hydrocarbon groups at least 1 and up to 20 carbon atoms and a cyclic anion that possesses a negatively charged group reactive with a gaseous electrophilic species, particularly carbon dioxide or sulfur dioxide. Methods for capturing a gaseous electrophilic species, such as $CO_2$ or $SO_2$, by contacting the gaseous electrophilic species with an ionic liquid are described. However, the methods and formulations employed for this purpose are beset with several drawbacks. A particular problem associated with ionic liquid capture materials is the high viscosity generated in these ionic liquids on absorbing $CO_2$, which adversely slows absorption kinetics, and hence, substantially increases operating costs.

U.S. Pat. No. 9,533,258 B2 describes a formulation and process for capturing $CO_2$ using an absorption mixture containing water, biocatalysts and a carbonate compound. The process includes contacting a $CO_2$ containing gas with the absorption mixture to enable dissolution and transformation of $CO_2$ into bicarbonate and hydrogen ions, thereby producing a $CO_2$ depleted gas and an ion rich solution, followed by subjecting the ion rich solution to desorption. The biocatalyst improves absorption of the mixture comprising carbonate compounds and the carbonate compound promotes the release of the bicarbonate ions from the ion rich solution during desorption, producing a $CO_2$ gas stream and an ion depleted solution.

Another invention, WO2013159228 A1 conveys techniques for treating $CO_2$ containing gas with an aqueous absorption solution containing carbonic anhydrase as well as an absorption compound, which may be a tertiary amino compound for an enzymatically enhanced flux of $CO_2$. The absorption compound may include MDEA, TEA, DEMEA, DMMEA, TIPA or DMgly. The techniques may provide concentrations to enhance the enzymatic catalysis and inhibit viscosifying of the absorption solution or enzyme denaturation that would lower the overall $CO_2$ absorption rate. The absorption may be conducted at a temperature between about 0° C. and about 80° C.

WO2011014955A1 discloses a formulation and a process for $CO_2$ capture, where a $CO_2$ containing gas is contacted with water, biocatalyst and an amino acid compound, enabling the dissolution and transformation of the $CO_2$ into bicarbonate ions and hydrogen ions, producing an ion rich solution and a $CO_2$ depleted gas. The amino acids may present slow absorption kinetics and have elevated stability such that absorption is enhanced in combination with the biocatalyst. The amino acid compound and the biocatalyst may be selected such that the active sites of the biocatalyst benefit from proton removal facilitated by the amino acid compounds, thus improving the $CO_2$ absorption. The major disadvantage of this process is the requirement of higher loading of the enzyme. Moreover, the stability of biocatalyst in harsh amine condition is challenging. The biocatalysts are subjected to easy denaturation and have low thermal stability.

The inventors of the present application have developed an improved system and process for capturing $CO_2$ that has higher selectivity and higher desorption of $CO_2$ to improve the overall efficiency of the process.

SUMMARY OF THE INVENTION

The present invention relates to a process for reduction of $CO_2$ emission particularly by selective $CO_2$ capture. The invention further relates a process which involves a bio-amine cluster system and catalyst for selective capturing of $CO_2$ from any gaseous stream.

The present invention in one of the embodiment, relates to a process for selective capture of $CO_2$ from gaseous mixture.

In another embodiment, the invention relates to a process for production of bio-amine cluster used selective capture of $CO_2$ from gaseous mixture.

In another embodiment invention provides a process for selective capture of $CO_2$ from gaseous mixture comprising of: (a) spraying a bio-amine cluster; (b) capturing $CO_2$ through bio-amine cluster; and (c) desorption of $CO_2$ through solar assisted electro de-amination.

In another embodiment, the invention provides a process for selective capture of $CO_2$ from gaseous mixture comprising use of a bio-amine cluster composed of: (i) an amine cluster; (ii) a cluster stabilizing agent; (iii) a cluster micelle stabilizing agent; and (iv) a carbonic anhydrase (CA) functionalized matrix in 0.05-0.2 wt % of total wt % of bio-amine cluster.

In another embodiment, the invention provides a process for selective capture of $CO_2$ from gaseous mixture comprising use of a carbonic anhydrase (CA) obtained from a source selected from the group consisting of *Bacillus thermoleovorans, Pseudomonas fragi, Bacillus stearothermophilus* and *Arthrobacter* sp.

In another embodiment, the invention provides a process for selective capture of $CO_2$ from gaseous mixture using an amine cluster comprising use of a quaternary Isobutylamine (IB) with amine terminated Poly(L-lactide) as the chelating agent.

In another embodiment, the invention provides a process for selective capture of $CO_2$ from gaseous mixture comprising use of a cluster stabilizing agent selected from the group comprising of Poly (ethylene glycol) diamine (PEGD), diamino butane, Urea, 1,6-Hexanediamine, Diethylenetriamine, N1,N1-Dimethylbenzene-1,2-diamine, 1, 3-Diaminopentane, Ethylenediamine.

In still another embodiment, the invention provides a process for selective capture of $CO_2$ from gaseous mixture comprising use of a cluster micelle stabilizing agent, which is a long chain alkyl amine or N-based alkyl amines and derivatives and is selected from the group consisting of N-[2-[(2-Aminoethyl) amino] ethyl]-9-octadecenamide (AMEO), n-Benzalkonium chloride (BAC), CnH(2n+1)-COO(CH2CH2O)12CH3, Polyoxythylene alkyl ether, n-Alkyltrimethyl ammonium surfactant, Potassium alkanoate, Dodecylpyridinium bromide, Octylglucoside, Sodium dodecyl sulfate, trans-Cinnamaldehyde, Sodium bis-(2-ethylhexyl)-sulfosuccinate, Cetylpyridinium chloride, Primary alcohol ethoxylate, Polyoxyethylene nonyl phenyl ether, Polyethylene glycol esters, Linoleate, Dodecylamine.

In another embodiment, the invention provides a process for selective capture of $CO_2$ from gaseous mixture comprising use of a poly (ethylene glycol) diamine (PEGD) as cluster stabilizing agent and N-[2-[(2-Aminoethyl) amino] ethyl]-9-octadecenamide (AMEO) as cluster micelle stabilizing agent.

In still another embodiment, the invention provides a process for selective capture of $CO_2$ from gaseous mixture comprising use of carbonic anhydrase functionalized matrix comprised of: (i) a porous matrix obtained by calcination of precipitates obtained by reacting $CaCl_2$ with tetraethylorthosilicate in presence of Pluronic F-127, cetyl trimethyl ammonium bromide, boric acid and $CO_2$; and (ii) a thermostable enzyme extracted from *Bacillus stearothermophilus*.

In another embodiment, the invention provides a process for selective capture of $CO_2$ from gaseous mixture comprising use of bio-amine cluster that is capable of desorption of $CO_2$.

Still in another embodiment, the present invention provides a process for production of bio-amine cluster for selective absorption of $CO_2$ comprising of: (i) synthesis of an amine cluster; and (ii) synthesis of a carbonic anhydrase (CA) functionalized matrix.

In another embodiment, the present invention provides a process for production of bio-amine cluster for selective absorption of $CO_2$ comprising steps of:

synthesizing the quaternary Isobutylamine (IB) by reacting $C_2$-$C_{10}$ alkalomine or hindered amine and HCl in equimolar concentrations in presence of amine terminated Poly(L-lactide) (ATPL) as a chelating agent;

incubating the reaction solution obtained from preceding step in ice bath for 30-60 minutes;

incubating the reaction solution obtained from preceding step at a temperature of 55-60° C. for 80-60 minutes and thereafter allowing to cool the reaction solution at room temperature;

removing excess water and HCl from the reaction solution obtained from preceding step to attain basic pH by using a rotary evaporator at 20-35° C.;

crystallizing the solution obtained from preceding step using equal volume of acetone and diethyl ether solvent at a volume ratio of 1:1;

separating and drying the solid crystalline layer obtained from preceding step at a room temperature under vacuum;

dissolving the solid crystalline substance obtained from preceding step in deionized water in a wt % of 30:70;

adding 0.5 mM of a cluster stabilizing agent selected from the group comprising Poly (ethylene glycol) diamine (PEGD), diamino butane, Urea, 1, 6-Hexanediamine, Diethylenetriamine, N1,N1-Dimethylbenzene-1,2-diamine, 1,3-Diaminopentane, Ethylenediamine;

stirring the solution obtained from preceding step for 20-40 minutes at room temperature;

adding 500 ppm of cluster micelle stabilizing agent to the solution obtained from preceding step wherein the cluster micelle stabilizing agent is selected from the group comprising N-[2-[(2-Aminoethyl) amino] ethyl]-9-octadecenamide (AMEO), n-Benzalkonium chloride (BAC), $C_nH_{(2n+1)}$—COO$(CH_2CH_2O)_{12}CH_3$, Polyoxythylene alkyl ether, n-Alkyltrimethyl ammonium surfactant, Potassium alkanoate, Dodecylpyridinium bromide, Octylglucoside, Sodium dodecyl sulfate, trans-Cinnamaldehyde, Sodium bis-(2-ethylhexyl)-sulfosuccinate, Cetylpyridinium chloride, Primary alcohol ethoxylate, Polyoxyethylene nonyl phenyl ether, Polyethylene glycol esters, Linoleate, Dodecylamine; and sonicating the solution obtained from preceding step for 2-10 minutes followed by stirring at room temperature for 15-30 minutes.

In another embodiment, the present invention provides a process for production of bio-amine cluster for selective absorption of $CO_2$ comprising use of $C_2$-$C_{10}$ alkalomine or hindered amine and HCl in aequimolar concentrations of 5 moles.

In another embodiment, the present invention provides a process for production of bio-amine cluster for selective absorption of $CO_2$ comprising, maintaining a temperature at 2-6° C. during reaction of $C_2$-$C_{10}$ alkalomine or hindered amine and HCl.

In another embodiment, the present invention provides a process for production of bio-amine cluster for selective absorption of $CO_2$ comprising use of ATPL in a concentration of 50 ppm.

In another embodiment, the present invention provides a process for production of bio-amine cluster for selective absorption of $CO_2$ comprising use of $C_2$-$C_{10}$ alkalomine or hindered amine selected from the group comprising of hydrochloride, sulfate, nitrate salt of Isobutyl amine, 2-amino-2-methyl-ipropanol, 2-(2-aminoethylamino)ethanol, 2-amino-2-hydroxymethyl-1,3-propanediol, N-methyl-diethanolamine, dimethylmonoethanolamine, diethylmonoethanolamine, triisopropanolamine, triethanolamine, trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine.

In another embodiment, the present invention provides a process for production of bio-amine cluster for selective absorption of $CO_2$ comprising use of cluster stabilizing agent is poly (ethylene glycol) diamine (PEGD) and cluster micelle stabilizing agent is N-[2-[(2-Aminoethyl) amino] ethyl]-9-octadecenamide (AMEO).

In another embodiment, the present invention provides a process for production of bio-amine cluster for selective absorption of $CO_2$ comprising synthesis of a carbonic anhydrase (CA) functionalized matrix comprises steps of:

adding porous matrix to an ethanol solution containing 0.5-2% v/v (3-Glycidyloxypropyl) trimethoxysilane and 0.5-2% v/v triethoxy-3-(2-imidazolin-1-yl) propylsilane;

incubating the suspension obtained from preceding step at 55-65° C. for 80-160 minutes with continuous stirring;

filtering and washing porous matrix from preceding step with deionized water and drying at room temperature to obtain a functionalized matrix;

suspending the functionalized matrix in a 50 mM sodium phosphate solution containing a thermo-stable carbonic anhydrase (CA);

stirring the suspension obtained from preceding step at 160-240 rpm for 80-160 minutes at room temperature to obtain a CA functionalized matrix; and filtering and washing CA functionalized matrix from preceding step with deionized water.

In another embodiment, the present invention provides a process for production of bio-amine cluster for selective absorption of $CO_2$ comprising use of CA obtained from a source selected from the group consisting of *Bacillus thermoleovorans*, *Pseudomonas fragi*, *Bacillus stearothermophilus* and *Arthrobacter* sp.

In another embodiment, the present invention provides a process for production of bio-amine cluster for selective absorption of $CO_2$ comprising use of CA having a pH tolerance in the range of 5-13, temperature tolerance in the range of 4-110° C. and salinity tolerance in the range of 0-6%.

In another embodiment, the present invention provides a process for production of bio-amine cluster for selective absorption of $CO_2$ comprising synthesis of a porous matrix comprising steps of:

preparing a solution of Pluronic F-127 (surfactant) and cetyl trimethyl ammonium bromide in deionized water and adding boric acid under stirring condition;

incubating the solution obtained from preceding step with continuous stirring for 10-30 minutes;

adding 0.5 M $CaCl_2$ to the solution obtained from preceding step and incubating with vigorous stirring for 15-45 minutes;

adding tetraethylorthosilicate drop wise to the solution obtained from preceding step and passing $CO_2$ for 10-20 minutes to obtain precipitate;

filtering and oven drying the precipitate obtained from preceding step; and calcining the dried precipitate obtained from preceding step at a temperature of 160-240° C. for 240-360 minutes to obtain the porous matrix.

DESCRIPTION OF THE ACCOMPANYING DRAWINGS

FIG. 1 illustrates the sequential preparation of the solvent system for $CO_2$ absorption and desorption.

Figure 2:
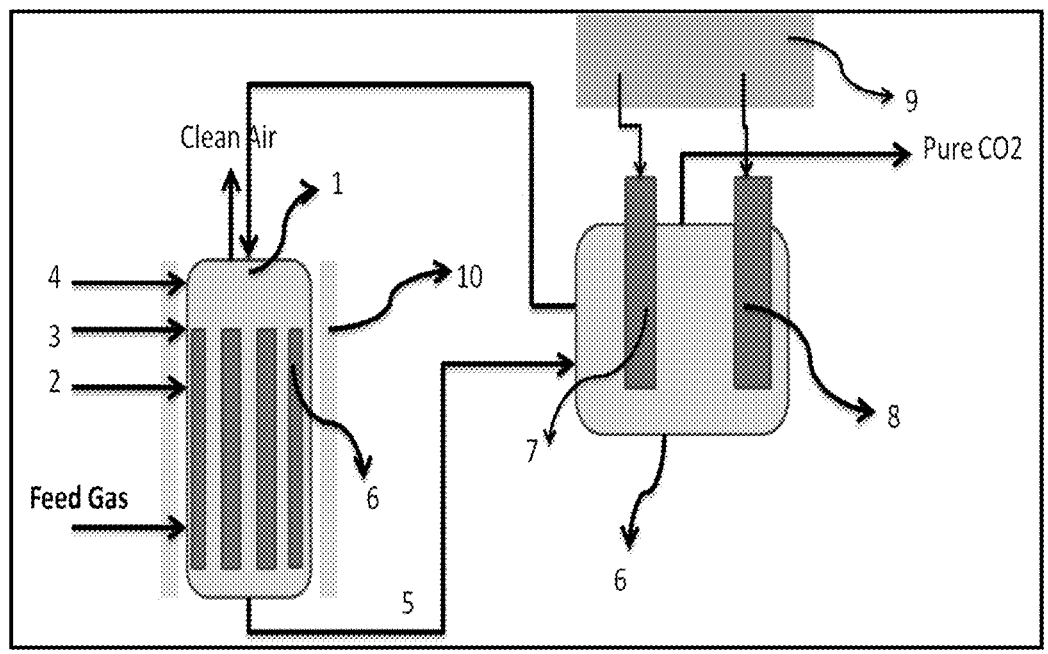

FIG. 2 illustrates the device for $CO_2$ capture and solar assisted electro deamination process. (1) $CO_2$ capture vessel (2) Dosing inlet of $C_2$-$C_{10}$ alkalomine in presence of a salt solution and chelating agent (3) Dosing inlet of cluster stabilizing solvent (4) Dosing inlet of cluster micelle agents (5) Transfer inlet of CO2 rich solvent (6) Immobilized bio-active catalysts (7) working electrode (8) counter electrode (9) electric supply unit to electrodes.

Figure 3:
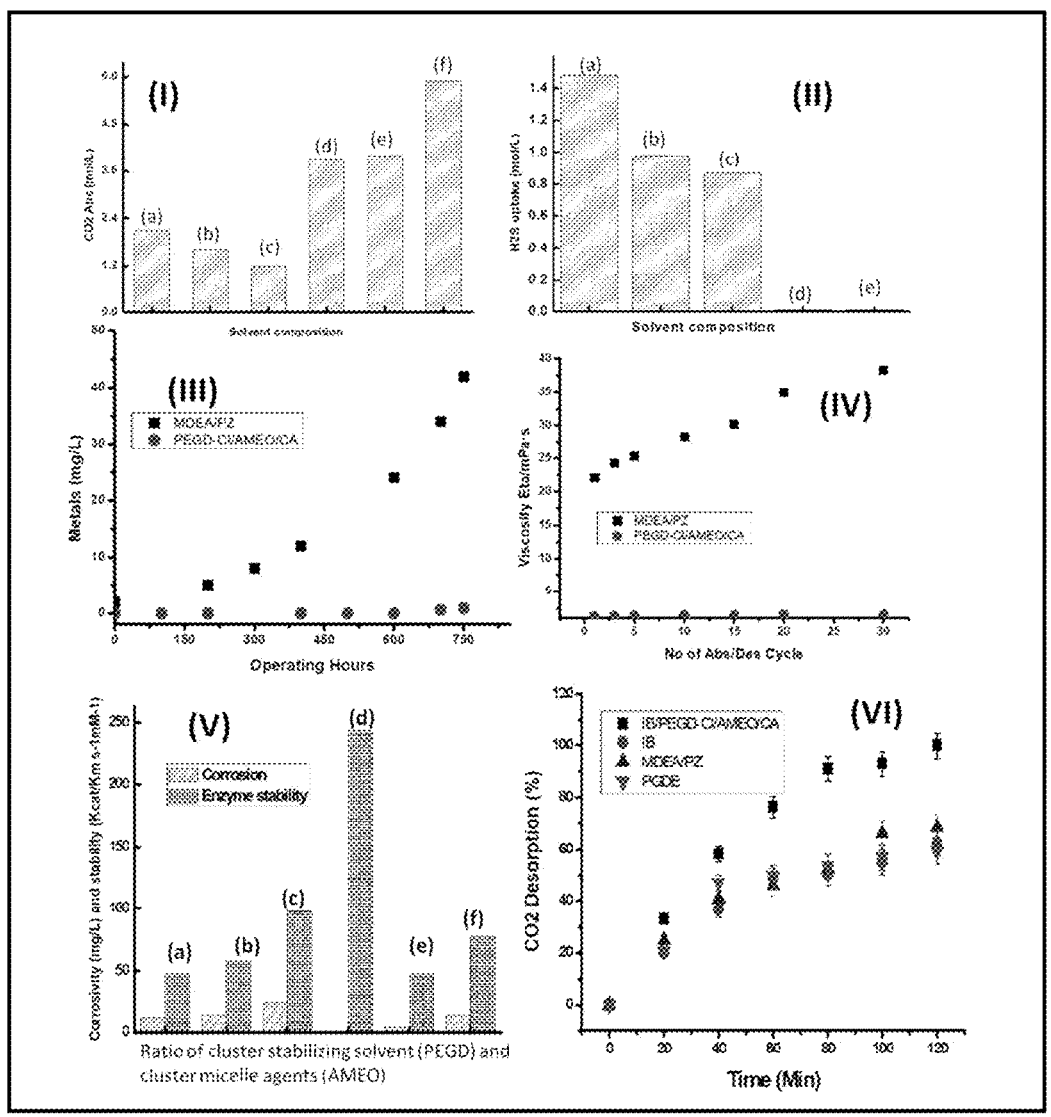

FIG. 3 is a consolidated representation of (I) $CO_2$ absorption by different solvent system (a) MDEA/PZ, (b) IB, (c) PEGD, (d) IB/PEGD-Cl, (e) IB/PEGD-Cl/AMEO, (f) IB/PEGD-Cl/AMEO/CA (II) H2S selectivity: (a) MDEA/PZ (b) IB, (c) PEGD, (d) IB/PEGD-Cl, (e) IB/PEGD-Cl/AMEO/CA (III) Corrosion behavior by bio-amine cluster (IV) Change of viscosity over cycles (V) Change in corrosion behaviour and enzyme stability by change in ratio of cluster stabilizing solvent (PEGD) and cluster micelle agents (AMEO) (a) PEGD:AMEO=1:0.1, (b) 1:0.5 (c) 1:1 (d) 1:2 (d) 1:4 (e) 1:5 (f) 1:6

DETAILED DESCRIPTION OF THE INVENTION

While the invention is susceptible to various modifications and/or alternative processes and/or solvent system, specific embodiment thereof has been shown by way of examples and will be described in detail below. It should be understood, however that it is not intended to limit the invention to the particular processes and/or solvent system disclosed, but on the contrary, the invention is to cover all modifications, equivalents, and alternative falling within the spirit and the scope of the invention as defined by the appended claims.

The figures and protocols have been represented where appropriate by conventional representations, showing only those specific details that are pertinent to understanding of the embodiments of the present invention and not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particulars and all details set forth herein are used in the context of some embodiments and therefore should not be necessarily taken as limiting factors to the attached claims. The attached claims and their legal equivalents can be realized in the context of embodiments other than the ones used as illustrative examples in the description below.

The present invention discloses a bio-amine cluster system for selective CO2 absorption from any mixed gas stream and desorption at low temperature. The hybrid solvent consists of an amine cluster formed by complexation of $C_2$-$C_{10}$ alkalomine/hindered amines in presence of a salt solution and chelating agent.

In accordance with the present invention, a process for the selective separation of $CO_2$ from a mixture of any sour or acidic gas streams is provided, said sour or acidic streams includes but is not limited to $H_2S$, $CO_2$, $CH_3$, CO, $SO_2$, $NO_2$, moisture, FCF or any other gases.

In accordance with the present invention, the process for selective $CO_2$ capture and regeneration comprises of the following steps.
1. Development of a solvent system including synthesis of at least one amine cluster by complexation of $C_2$-$C_{10}$ alkalomine in presence of a salt solution and chelating agent. Addition of at least one cluster stabilizing solvent. Addition of at least one cluster micelle agents.
2. Development of a biocatalyst or biomimetic complex including isolation of thermostable enzyme having ability to form stable bonding with the cluster micelle agents and having pH stability in both acidic and alkaline medium. Synthesis of stable matrix system and encapsulation of bio-active catalysts.
3. Addition of at least one bio-amine cluster that has been formulated by a suitable combination of amine cluster (1) and matrix encapsulated thermostable enzyme having ability to form stable bonding with the cluster micelle agents.
4. Selective $CO_2$ absorption by Bio-amine cluster at different condition. Viscosity monitoring after $CO_2$ loading and Corrosion monitoring.
5. Desorption of $CO_2$ and regeneration amine has been carried out by solar assisted electro deamination followed by recycling of $CO_2$ lean solvent.

The amine cluster was synthesized from $C_2$-$C_{10}$ alkalomine or hindered amine solvents used in one or more process steps of the present invention include but are not limited to one or more of the following: The hydrochloride, sulfate, nitrate salt of Isobutyl amine, 2-amino-2-methyl-ipropanol, 2-(2-aminoethylamino)ethanol, 2-amino-2-hydroxymethyl-i,3-propanediol, N-methyldiethanolamine, dimethylmonoethanolamine, diethylmonoethanolamine, triisopropanolamine and triethanolamine), trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3, 3-dimethylbutylamine, N,N-dimethylbutylamine.

In accordance with the present invention, the ratio of salts can be varied from 1:0 (by volume) to 1:5; however the total concentration will be at 10-30 wt %. The chelating agent consists of amine terminated Poly(L-lactide) average $M_n$ 2,500. The concentration will be varied between 50-100 ppm.

In an embodiment of the present invention the cluster stabilizing solvent: Poly (ethylene glycol) diamine, diamino butane, Urea, 1, 6-Hexanediamine, Diethylenetriamine, N1, N1-Dimethylbenzene-1, 2-diamine, 1, 3-Diaminopentane, Ethylenediamine. The concentration of hydrogen bonding solvent may be varied from 0 to 0.5 mM.

In another aspect of the present invention, the cluster micelle agents can be long chain alkyl amine or N-based alkyl amines and derivatives, N-[2-[(2-Aminoethyl) amino] ethyl]-9-octadecenamide, n-Benzalkonium chloride (BAC), $C_nH_{(2n+1)}$—COO$(CH_2CH_2O)_{12}CH_3$, Polyoxythylene alkyl ether, n-Alkyltrimethyl ammonium surfactant, Potassium alkanoate, Dodecylpyridinium bromide, Octylglucoside, Sodium dodecyl sulfate, trans-Cinnamaldehyde, Sodium bis-(2-ethylhexyl)-sulfosuccinate, Cetylpyridinium chloride, Primary alcohol ethoxylate, Polyoxyethylene nonyl phenyl ether, Polyethylene glycol esters, Linoleate, Dodecylamine, The concentration of the stabilizer can be varied form 0-500 ppm.

In another embodiment of the present invention, the matrix for biocatalyst encapsulation composed of hieratical high surface area porous calcium carbonate functionalized with borate, ZnO, NiO, biomimetic complex of Zn and Ni, porous polymeric gel. The matrix amount was varied from 0.1-0.5 g/L in the amine cluster.

In accordance to present invention, the enzyme is carbonic anhydrase (CA) or related enzymes. In accordance to present invention, the enzyme compositions contain CA from *Bacillus thermoleovorans* IOC-S3 (MTCC 25023) and/or *Pseudomonas fragi* IOC S2 (MTCC 25025), and/or *Bacillus stearothermophilus* IOC S1 (MTCC 25030) and/or *Arthrobacter* sp. IOC-SC-2 (MTCC 25028).

In accordance with present invention, the CA has pH tolerance in the range of 5-13, temperature tolerance 4-100° C. and salinity tolerance 0-6%. The CA from *Bacillus stearo*-

*thermophilus* IOC S1 (MTCC 25030) has higher $CO_2$ dehydration activity. It is pH tolerance in the range of 3-13, temperature tolerance 0-110 degree C. and salinity tolerance 0-5%. The CA from *Bacillus thermoleovorans* IOC-S3 (MTCC 25023), *Pseudomonas fragi* IOC S2 (MTCC 25025), *Bacillus stearothermophilus* IOC S1 (MTCC 25030), *Arthrobacter* sp. IOC-SC-2 (MTCC 25028) have both CO2 hydration & dehydration activity. The concentration of the crude biocatalyst can be varied from 0 to 150 mg per g of immobilization matrix.

In another embodiment, the biomimetic catalysts consist of tripodal ligand system and macro-cyclic ligand systems can be used. The ligands mainly consist of 1-(3-Aminopropyl)-2-methyl-1H-imidazole and glutaraldehyde, 3-(2-Ethyl-1H-imidazol-1-yl)propan-1-amine and glutaraldehyde, 2-(4,5-Dimethyl-1H-imidazol-1-yl)ethanamine dihydrochloride and glutaraldehyde, 3-(2-isopropyl-imidazol-1-yl)-propylamine and glutaraldehyde. The metal can be varied as Zn, Cu, Ni, Cd or Ln. The immobilized biomimetic complex can be altered from 0 to 300 mg/g of the immobilization matrix.

In another embodiment, it was found that the bio-amine cluster shows higher $CO_2$ loading activity with intermittent dosing of cluster stabilizing solvent. With dosing rate of 0.3 ml-0.5 ml/min, there is an enhancement of 5-6% loading of $CO_2$. In yet another embodiment, it was observed that the bio-amine cluster shows lower $H_2S$ selectivity and higher $CO_2$ selectivity with controlled addition of chelating agent consists of amine terminated Poly(L-lactide) average $M_n$ 2,500. With dosing rate of 0.05 ml-0.1 ml/min, there is a decrease of 5-6% loading of $H_2S$ and 7-8% increase in the $CO_2$ capture.

In an embodiment, the stabilizer described herein provides resistance to an increase in viscosity during absorption of the gaseous species. The stabilize concentration can be varied depending on the % of $CO_2$ in the feed gas. For example, for every increase in 10% of $CO_2$, 100 ppm stabilizer needs to be added to maintain the viscosity between 1.33 and 1.75 η/mPa·s. In some embodiments, the viscosity is maintained or may even decrease.

In yet another embodiment, different $CO_2$ sources have been used for the capture. In these processes, carbon dioxide-containing flue gas, or process gas or gas from bio-methanation plants can be used. The $CO_2$ concentration can be varied from 200 ppm to 30% in the source gas. The resulting gas can be passed through the solvent medium through in any suitable device forming the fine dispersion of gas result in an increase in contact area. The $CO_2$ may be sparged in micro-bubble or nano-bubble size.

In another embodiment, the pressure of $CO_2$ can vary from 0.1 bar to 0.3 bar and temperature can be varied between 20-70° C. In an aspect of the present invention, the corrosion activity was studied for 0-60 days in a stainless vessel by analysis the leaching metal ion in the solvent. The $CO_2$ desorption was carried out by thermal or solar assisted electro desalination method.

In an aspect of the present invention, the viscosity of the bio-amine cluster having viscosity of 1.67 mPa·s has been analyzed for a period of 100 cycles of $CO_2$ absorption and desorption. After 100 cycles the viscosity of bio-amine cluster was found to be 1.65 mPa s. The result indicates that there is no change in viscosity after multiple $CO_2$ absorption and desorption cycle.

In another embodiment, the amine regeneration takes place using solar assisted electrolysis cell. The solar assisted electrolysis cell includes an electrochemical cell, working electrode, a counter electrode, a reference electrode, a chelating salt, a solar panel that supply an electric potential to the solution in the electrolysis. The electrolysis cell can be made up of insulating material including glass, polyester, PVC. The working electrode can compose of a 2D material coated stainless steel mesh. The 2D material coated on stainless steel mesh can be porous graphene, MWCNT, $gC_3N_4$ or $MoS_2$. The electrodes were synthesized by sintering the 2D material on the surface of stainless steel mesh along with a conducting polymer. The conducting polymer can be poly(pyrrole)s (PPY), polycarbazoles, polyindoles, polyazepines, polyanilines (PANI). The counter electrode can be graphite or copper with silver as the reference electrode. The chelating salt can be a salt of any elements in group 2 including beryllium, magnesium, calcium, strontium, barium, The concentration of salts can be varied from 10-500 ppm during electrolysis.

Having described the basic aspects of the present invention, the following non-limiting examples illustrate specific embodiment thereof.

Example 1

Selective $CO_2$ capture by amine cluster obtained from quaternary Isobutyl amine with amine terminated Poly(L-lactide) as the chelating agent, cluster stabilizing solvent as Poly (ethylene glycol) diamine, cluster micelle agents N-[2-[(2-Aminoethyl) amino] ethyl]-9-octadecenamide and by addition of biocatalyst immobilized on polyamine functionalized porous $CaCO_3/BO_3/Zn$.

Synthesis of Bio-Amine Cluster (a) To synthesize the bio-amine cluster first the quaternary Isobutylamine (IB) was synthesized by the following procedure. Typically, 5 mol (200 ml) of solvent was taken in a round-bottomed flask and kept at 4° C. using the ice bath. Equimolar concentration of HCl (200 ml) and 50 ppm amine terminated Poly(L-lactide) (ATPL) as a chelating agent was added to it from the corner walls of the flask in a chemical hood. The solution was continued to be kept in the ice bath for another 45 minutes. The mixture was then heated at 60° C. for two hours and the kept at room temperature to cool down. The excess water and HCl was removed using a rotary evaporator at 25-30° C. till basic pH was obtained. After evaporation, remaining mixture was transferred to a separating funnel containing same volume of acetone and diethyl ether solvent at volume ratio of 1:1. The solution was mixed thoroughly resulting in the crystal formation with a liquid layer. The solid crystalline layer (pale white) was separated and dried at room temperature under vacuum.

(b) 30 wt % of the above solid was dissolved in deionized water followed by addition of 0.5 mM of Poly (ethylene glycol) diamine (PEGD) as cluster stabilizing solvent. The solution was stirred for 30 minutes at room temperature. To the resulting solution 500 ppm N-[2-[(2-Aminoethyl) amino] ethyl]-9-octadecenamide (AMEO) has been added as cluster micelle stabilizer. The solution was then sonicated for 5 minutes followed by stirring at room temperature for another 20 minutes and designated as amine cluster.

(c) The matrix encapsulated biocatalyst was synthesized as follows: Typically, surfactant Pluronic F-127 (0.2 g) and cetyl trimethyl ammonium bromide (0.2 g) were dissolved 100 ml of deionized water. 0.05 g of boric acid was inserted under stirring condition. After 20 minutes of stirring, 0.5 M $CaCl_2$ was added and vigorously stirred for another 30 minutes. 10 ml of tetraethylorthosilicate was added dropwise and $CO_2$ (99.9%) was passed for a period of 15 minutes at 200 ml/min. The precipitate obtained is then filtered and oven dried. After complete dryness, the material was calcined at 200° C. for 5 hours to obtain the porous matrix.

(d) The thermostable enzyme was extracted from *Bacillus stearothermophilus* IOC S1 (MTCC 25030).

(e) The enzyme encapsulated matrix by the following procedure: Typically, 5 g of the matrix was inserted into a 2 necked flask containing 10 ml of ethanol and 0.1 ml of (3-Glycidyloxypropyl) trimethoxysilane and 0.1 ml of triethoxy-3-(2-imidazolin-1-yl) propylsilane. The sample was stirred for 2 hours at 60° C., filtered, washed 4 times with deionized water and dried at room temperature. 1 g of this functionalized supports is added to 20 ml 50 mM sodium phosphate pH 7.0 of containing 2 mg/ml crude thermo-stable CA and gently stirred (200 rpm) at room temperature for 2 hours. The CA functionalized matrix was filtered and washed 4 times with deionized water. The filtrate was analyzed via Bradford protein assay to calculate the residual enzyme. A loading of 147±3 mg/g of the matrix was obtained.

(f) The bio-amine cluster was formulated by the addition of 0.1 wt % of enzyme encapsulated matrix obtained by the process described in step 'e' to the amine cluster obtained in the process 'b' of the described example.

Carbon Dioxide Absorption (a) Gravimetric analysis: For $CO_2$ absorption measurements of the bio-amine cluster, $CO_2$ gas was flown into a reactor (100 mL) containing 20 g of solvent at a flow rate of 20 mL min$^{-1}$. The weight percent of $CO_2$ absorbed was determined by weighing the solvent at a regular interval using an electronic balance with an accuracy of ±0.1 mg. The immobilized biocatalyst amount was fixed 0.1 g/100 ml of amine cluster.

(b) The time dependent $CO_2$ uptakes of amine cluster with and without biocatalyst were measured at 30° C. and 1 atmospheric pressure using the gravimetric method. FIG. 3(I) particularly demonstrates the following points: Firstly, all of these solvent combinations exhibited $CO_2$ uptakes to different extents. When the commercially used solvent like Methyl diethanolamine (N-methyldiethanolamine) and piperazine (30% MDEA/PZ) was used, a $CO_2$ uptake of 2.1 mol/l was observed after 30 minutes. Further, when the 30% bio amine cluster was used, a maximum $CO_2$ uptake of 5.9 mol/l was observed. The extent of $CO_2$ uptake by individual components composed in Bio-amine cluster was provided in FIG. 3(a). Two most important observations were:

a) The individual components present in bio amine cluster shows a $CO_2$ uptake trend as flows: PEGD<IB<MDEA/PZ<IB/PEGD-Cl<IB/PEGD-Cl/AMEO<IB/PEGD-Cl/AMEO/CA. The results concluded that a maximum $CO_2$ capture can be observed by the suitable combination of different components present in the bio-amine cluster.

b) The uptake amount was increased to 5.45 mol/l wt % when the 0.1 wt % enzyme loaded matrix was used in the amine cluster.

Selectivity Study of Bio Amine Cluster (a) The selectivity of bio amine cluster toward $H_2S$ was carried out at 25° C. with an $H_2S$ concentration of 500 ppm (balance $N_2$). The experiment was carried out by a procedure as described for $CO_2$ absorption measurements with the $H_2S$ gas having a flow rate of 200 ml/min. The $H_2S$ uptake was analyzed by gravimetric analysis for a period of 1.25 hours. From the results, it was found that with MDEA/PZ 1.48 mol/l of $H_2S$ capture was observed, whereas IB-PEGD-Cl/AMEO/CA shows almost no selectivity towards $H_2S$. FIG. 3(II) gives the selectivity of different components of bio amine cluster towards $H_2S$.

Stability of Bio Amine Cluster in Operation Condition (a) The corrosion behavior of the bio amine cluster has been observed from the metal leaching of the container material. Experiments were performed for a continuous 750 hours and the total metal contents were analyzed by inductively coupled plasma atomic emission spectroscopy ICPAES. It has been found that (FIG. 3.III) for MDEA/PZ, there was a leaching of 42 ppm of metal after 750 hours of operation, whereas in IB-PEGD-Cl/AMEO/CA, only 0.9 ppm metal was leached. This clearly indicates that IB-PEGD-Cl/AMEO/CA showed very low corrosion activity.

(b) The viscosity of the IB-PEGD-Cl/AMEO/CA was measured for 30 numbers of consecutive absorption and desorption cycles and compared with that of MDEA/PZ. It has been observed that the viscosity of MDEA/PZ increases after each absorption and desorption cycles and reaches to 38 eta/mPa·s, whereas the viscosity of IB-PEGD-Cl/AMEO/CA remains almost constant after 30 cycles of operation.

(c) The enzymatic stability has been studied using p-NPA hydrolysis measurement in the different solvent system. The encapsulated enzyme was immersed in the solvent for 30 days and then the catalytic activity of the enzyme ($K_{cat}/K_M$) was evaluated. It has been observed that has and It has been found that the enzyme is highly stable in IB-PEGD-Cl/AMEO and IB-PEGD-Cl solution with $K_{cat}/K_M$ value as 233 and 278 s−1mM−1 respectively. Whereas, the CA lost its activity completely in MDEA.PZ solution after 30 days.

Further, it was found that the corrosion behaviour and enzyme stability was highly dependent on the ratio of cluster stabilizing solvent (PEGD) and cluster micelle agents (AMEO) (FIG. 3.V). The maximum CA stability and lowest corrosion behavior were observed when PEGD:AMEO was 1:3.

Example 2

$CO_2$ Desorption Form Captured Solution as Described in Example 1.

Solar assisted electro deamination process: Desorption of $CO_2$ was carried out in a solar assisted electrochemical container. The container was filled with the $CO_2$ rich solution as obtained from example 1 along with 0.01 mM of $MaCl_2$ was added to the solution as the chelating agent. The container is attached to a counter electrode and a working electrode. A solar panel is used to provide the potential to the electrodes. A switch has been used to alter the potential of both the electrodes.

Electrode Design for Solar Assisted Electro Deamination Process

The working electrode can compose of a 2D material coated stainless steel mesh. Typically, a stainless steel mesh was washed in HCl (0.5 M) for 2 hours and then washed with deionized water for 3 times and dried in oven at 60° C. for 12 hours. 2 mg of powder of porous graphene was mixed with Poly(1,8-Diaminonaphthalene) (0.5 wt. %) to form a paste. The paste was then coated on the surface of stainless steel mesh to produce uniform films, followed by pressing with a presser to fabricate the electrode. After drying at 60° C., the electrode was used as the anode for the solar assisted electro deamination process.

CO2 Desorption and Amine Regeneration
  (a) The bio-amine cluster forms unstable complexes with the magnesium ion in the solution resulting in desorption of carbon dioxide. Switching between positive and negative potentials ensures the oxidation and reduction of the metal ion.
  (b) The voltage was switched between −1 to +1 V. the potential was altered in 5 minutes interval for a period of 2 hours. The gas generated was collected and analyzed for GC analysis.
  (c) In case of amine cluster with biocatalyst shows 1.6 times higher desorption comparison to the neat amine cluster FIG. 3 (VI).

The invention claimed is:

1. A process for selective capture of $CO_2$ from a gaseous mixture, the process comprising:
  synthesizing an amine cluster by complexation of a $C_2$-$C_{10}$ alkalomine in presence of a salt solution and a chelating agent;
  adding a cluster stabilizing agent and a cluster micelle stabilizing agent to the amine cluster;
  isolating a thermostable enzyme having an ability to bond with the cluster micelle agent, wherein the thermostable enzyme has a pH stability in acidic and alkaline media;
  synthesizing a carbonic anhydrase (CA) functionalized matrix to encapsulate the thermostable enzyme;
  adding the amine cluster to the matrix system to form a solvent system;
  loading a reactor with the solvent system;
  passing the gaseous mixture through the reactor to enable the solvent system to absorb the $CO_2$ from the gaseous mixture to form a $CO_2$ rich solvent system; and
  passing the $CO_2$ rich solvent system through a solar assisted electrochemical cell wherein the $CO_2$ is desorbed from the solvent system to obtain pure $CO_2$.

2. The process as claimed in claim 1, wherein the amine cluster comprises a quaternary Isobutylamine (IB) with amine terminated Poly(L-lactide) as the chelating agent.

3. The process as claimed in claim 1, wherein the cluster stabilizing agent is selected from the group consisting of Poly (ethylene glycol) diamine (PEGD), diamino butane, Urea, 1,6-Hexanediamine, Diethylenetriamine, N1,N1-Dimethylbenzene-1,2-diamine, 1, 3-Diaminopentane, and Ethylenediamine.

4. The process as claimed in claim 1, wherein the cluster micelle stabilizing agent is a long chain alkyl amine or N-based alkyl amines and derivatives and is selected from the group consisting of N-[2-[(2-Aminoethyl) amino] ethyl]-9-octadecenamide (AMEO), n-Benzalkonium chloride (BAC), CnH(2n+1)-COO(CH2CH2O)12CH3, Polyoxythylene alkyl ether, n-Alkyltrimethyl ammonium surfactant, Potassium alkanoate, Dodecylpyridinium bromide, Octylglucoside, Sodium dodecyl sulfate, trans-Cinnamaldehyde, Sodium bis-(2-ethylhexyl)-sulfosuccinate, Cetylpyridinium chloride, Primary alcohol ethoxylate, Polyoxyethylene nonyl phenyl ether, Polyethylene glycol esters, Linoleate, and Dodecylamine.

5. The process as claimed in claim 1, wherein the cluster stabilizing agent is poly (ethylene glycol) diamine (PEGD) and the cluster micelle stabilizing agent is N-[2-[(2-Aminoethyl) amino] ethyl]-9-octadecenamide (AMEO).

6. The process as claimed in claim 1, wherein the carbonic anhydrase functionalized matrix comprises a porous matrix obtained by calcination of precipitates obtained by reacting $CaCl_2$ with tetraethylorthosilicate in presence of Pluronic F-127, cetyl trimethyl ammonium bromide, boric acid, and $CO_2$.

7. The process as claimed in claim 1, wherein the thermostable enzyme is extracted from *Bacillus stearothermophilus*.

8. The process as claimed in claim 1, wherein synthesizing the amine cluster comprises:
  synthesizing quaternary Isobutylamine (IB) by reacting $C_2$-$C_{10}$ alkalomine or hindered amine and HCl in equimolar concentrations in presence of amine terminated Poly(L-lactide) (ATPL) as the chelating agent to obtain a reaction solution;
  incubating the reaction solution in an ice bath for 30-60 minutes and at a temperature in a range of 55-60° C. for 60-80 minutes and thereafter allowing to cool the reaction solution at room temperature;
  removing excess water and HCl from the reaction solution to attain a basic pH by using a rotary evaporator at a temperature in a range of 20-35° C.;
  crystallizing the reaction solution using an equal volume of acetone and diethyl ether solvent at a volume ratio of 1:1 to obtain a solid crystalline layer;
  separating and drying the solid crystalline layer at room temperature under vacuum;
  dissolving the solid crystalline layer in deionized water in a weight ratio of 30:70;
  adding 0.5 mM of the cluster stabilizing agent to obtain a solution;
  stirring the solution for 20-40 minutes at room temperature;
  adding 500 ppm of cluster micelle stabilizing agent to the solution; and
  sonicating the solution for 2-10 minutes followed by stirring at room temperature for 15-30 minutes to obtain the amine cluster.

9. The process as claimed in claim 1, wherein synthesizing a carbonic anhydrase (CA) functionalized matrix comprises:
  synthesizing a porous matrix;
  adding the porous matrix to an ethanol solution containing 0.5-2% v/v (3-Glycidyloxypropyl) trimethoxysilane and 0.5-2% v/v triethoxy-3-(2-imidazolin-1-yl) propylsilane to obtain a suspension;
  incubating the suspension at 55-65° C. for 80-160 minutes with continuous stirring;
  filtering and washing the suspension with deionized water and drying at room temperature to obtain a functionalized matrix;
  suspending the functionalized matrix in a 50 mM sodium phosphate solution containing a thermo-stable carbonic anhydrase (CA);
  stirring the functionalized matrix at 160-240 rpm for 80-160 minutes at room temperature to obtain a CA functionalized matrix; and
  filtering and washing the CA functionalized matrix with deionized water.

10. The process as claimed in claim 9, wherein synthesizing the porous matrix comprises:
  preparing a solution of Pluronic F-127 (surfactant) and cetyl trimethyl ammonium bromide in deionized water and adding boric acid under stirring;
  incubating the solution with continuous stirring for 10-30 minutes;
  adding 0.5 M $CaCl_2$) to the solution obtained and incubating with vigorous stirring for 15-45 minutes;

adding tetraethylorthosilicate drop wise to the solution and passing $CO_2$ for 10-20 minutes to obtain a precipitate;

filtering and oven drying the precipitate; and calcining the dried precipitate at a temperature of 160-240° C. for 240-360 minutes to obtain the porous matrix.

11. The process as claimed in claim 1, wherein the gaseous mixture comprises carbon dioxide-containing flue gas, a process gas, or a gas from bio-methanation plants.

12. The process as claimed in claim 11, wherein the $CO_2$ concentration in the gaseous mixture is in a range of 200 ppm to 30 vol % in the source gas.

13. The process as claimed in claim 1, wherein the gaseous mixture is sparged into the reactor as a fine dispersion having bubbles of a micro or a nano size.

14. The process as claimed in claim 1, wherein the gaseous mixture is passed through the reactor at a pressure in a range of 0.1 to 0.3 bar and at a temperature in a range of 20-70° C.

15. The process as claimed in claim 1, wherein the solar assisted electrochemical cell comprises an electrochemical cell, a working electrode, a counter electrode, a reference electrode, a chelating salt, and a solar panel.

16. The process as claimed in claim 15, wherein the working electrode comprises a 2D material coated stainless steel mesh, wherein the 2D material is porous graphene, MWCNT, $gC_3N_4$, or $MoS_2$.

17. The process as claimed in claim 16, wherein the working electrode is synthesized by sintering the 2D material on a surface of the stainless steel mesh along with a conducting polymer, and wherein the conducting polymer is poly(pyrrole)s (PPY), polycarbazoles, polyindoles, polyazepines, polyanilines (PANI).

18. The process as claimed in claim 15, wherein the counter electrode is graphite or copper, and wherein the reference electrode is silver.

19. The process as claimed in claim 15, wherein the chelating salt is a salt of elements of Group 2 comprising beryllium, magnesium, calcium, strontium, barium, and wherein the concentration of the salts is in a range of 10-500 ppm.

* * * * *